(12) United States Patent
Cecchetti

(10) Patent No.: US 12,076,430 B2
(45) Date of Patent: Sep. 3, 2024

(54) HAIR DYE

(71) Applicants: FABBRICA ITALIANA COSMETICA S.R.L., Otricoli (IT); Danilla Marii, Marino (IT)

(72) Inventor: Gianpiero Cecchetti, Rome (IT)

(73) Assignee: FABBRICA ITALIANA COSMETICA S.R.L., Otricoli (IT)

( * ) Notice: Subject to any disclaimer, the term of this patent is extended or adjusted under 35 U.S.C. 154(b) by 517 days.

(21) Appl. No.: 17/600,852

(22) PCT Filed: Mar. 7, 2020

(86) PCT No.: PCT/IT2020/050078
§ 371 (c)(1),
(2) Date: Oct. 1, 2021

(87) PCT Pub. No.: WO2020/202231
PCT Pub. Date: Oct. 8, 2020

(65) Prior Publication Data
US 2022/0151895 A1  May 19, 2022

(30) Foreign Application Priority Data
Apr. 2, 2019  (IT) .................. 102019000004921

(51) Int. Cl.
A61K 8/41 (2006.01)
A61K 8/44 (2006.01)
A61K 8/60 (2006.01)
A61Q 5/10 (2006.01)

(52) U.S. Cl.
CPC .............. *A61K 8/41* (2013.01); *A61K 8/44* (2013.01); *A61K 8/60* (2013.01); *A61Q 5/10* (2013.01); *A61K 2800/4324* (2013.01); *A61K 2800/522* (2013.01)

(58) Field of Classification Search
None
See application file for complete search history.

(56) References Cited

U.S. PATENT DOCUMENTS

2008/0196174 A1   8/2008 Schmenger et al.

OTHER PUBLICATIONS

International Search Report and Written Opinion of the ISA for PCT/IT2020/050078 dated Sep. 23, 2020, 10 pages.

*Primary Examiner* — Kyung S Chang
(74) *Attorney, Agent, or Firm* — NIXON & VANDERHYE

(57) ABSTRACT

Disclosed is the field of cosmetic products, in particular, a hair dye, of the permanent coloring type, including: a mixture including primary dyes, couplers, at least one alkalizing substance, a buffer substance, an antioxidant substance; and at least one oxidizing agent. The alkalizing substance is contained in an alkaline solution including: tri-N-propylamine; arginine; water; and an alkalizing agent selected from glucamine and bis (3-aminopropyl) dodecylamine, where the pH value of the alkaline solution is ≥9.5.

7 Claims, No Drawings

HAIR DYE

This application is the U.S. national phase of International Application No. PCT/IT2020/050078 filed Mar. 27, 2020 which designated the U.S. and claims priority to IT Patent Application No. 102019000004921 filed Apr. 2, 2019, the entire contents of each of which are hereby incorporated by reference.

TECHNICAL FIELD OF APPLICATION

The present invention relates to the field of cosmetic products.

In particular, the present invention concerns a hair dye of the permanent coloring type.

PRIOR ART

Permanent dyes contain various compounds capable of reacting with one another to give colored polymers. On their own, these compounds are not colored but acquire this property only after a chemical reaction in situ, hence inside the hair.

The formulations of permanent dyes available on the market are, in principle, composed as follows:
a first part containing the primary dyes, the couplers, an alkalizing agent, buffer substances to maintain an alkaline pH, and an antioxidant to prevent oxidation of the dyes;
a second part instead containing oxidizing agents such as hydrogen peroxide, pure or with the addition of urea.

Primary dyes are in truth not actual dyes, but dye precursors. The conversion of these precursors into dyeing substance takes place following oxidation and condensation processes. Dye precursors penetrate the fibers of the hair to reach the cortex, aided in this by swelling of the hair achieved due to the presence of alkalizing substances. The oxidizing agents instead promote the formation of colored pigments giving rise to colored molecules with high molecular weight that will remain trapped in the hair structure, giving it the desired color.

Currently, the most prevalently used alkalizing agents are ammonia and monoethanolamine.

Monoethanolamine, also called ethanolamine and abbreviated with MEA, is a chemical compound produced industrially through the reaction of ethylene and ammonia.

As mentioned above, ammonia and monoethanolamine are two alkaline substances that, without altering the pH, act on the outer part of the hair, dilating it to allow the color to penetrate.

In particular, ammonia causes the hair to become alkaline with a very strong peak during the first few minutes after application, the step in which the dye requires the most help to penetrate the hair. This is why it is very effective during dyeing and gives optimal results.

However, the use of ammonia and monoethanolamine in hair dyes has limits and drawbacks.

As ammonia is a gas, it is extremely volatile. If on the one hand the environment in which the hair undergoes processing is extremely comfortable due to evaporation of the ammonia, on the other hand its volatility causes an unpleasant pungent smell and, in cases of prolonged exposure it can be harmful to health. When the gas is released into the air it causes problems for the upper and lower respiratory tract and the eyes, producing watering, reddening, sneezing, etc.

Moreover, ammonia does not bond easily with water: this prevents the total removal of residues of the substance in the washing step and at times causes itching.

On the contrary, monoethanolamine is not volatile and does not have unpleasant odors. However, its non-volatility means that the alkalinity remains constant during processing of the dye, creating a less comfortable environment for the hair.

Monoethanolamine is sensitive to the environmental temperature, making it more fluid, and hence more active, in summer, when it tends to remain inside the hair structure due to its oil-like character, which delays removal from the hair structure and consequently causing possible hydrolysis, to the detriment of this structure.

Moreover, monoethanolamine can cause problems on the scalp due to its physical nature, according to which it is difficult to completely disperse/solubilize it in the active mass applied to dye the hair; consequently by remaining on the scalp, the part of monoethanolamine not adequately dispersed/solubilized gives rise to itching, burning, redness, etc.

The document US 2008/196174 A1 discloses a hair dye comprising:
a mixture comprising primary dyes, couplers, at least one alkalizing substance, a buffer substance, an antioxidant substance;
at least one oxidizing agent.

Said alkalizing substance is contained in an alkaline solution with a pH value ranging from 9 to 11, which comprises tripropanolamine.

This substance is a derivative of propane, has a relatively low alkalinity and is a heavy amine that acts poorly and slowly, offering weak coverage of the hair and requires to be integrated with other alkalizing substances such as ammonia or ethanolamine.

PRESENTATION OF THE INVENTION

The main object of the present invention is to provide a new hair dye that overcomes the aforesaid negative factors, and therefore performs highly from the viewpoint of hair coloration, without being aggressive or harmful towards the hair or scalp, or towards the environment.

These and other objects are achieved with the hair dye according to the main independent claim.

Further preferred methods of formulating the hair dye according to the invention will be apparent from the remaining dependent claims.

In relation to products known in the art, the hair dye of the invention is a combination of non-invasive alkalizing substances which act in synergy to obtain, in the dye mixture, the correct alkalinity.

Within this mixture, by varying time by time the amounts of the alkaline parts present, different variants thereof can be obtained.

The main advantages obtained with the use of the alkaline compound according to the invention are many.

The alkaline expression of the compound has an excellent performance within the dye, notwithstanding the lower level of alkalinity.

Moreover, tests conducted advantageously show total elimination of the alkaline residues and this leads us to believe that a varied use of alkalizing agents is successful for their elimination compared with the conventional use of a single alkalizing component, whether this is ammonia or monoethanolamine.

Advantageously, the coloring obtained with the dye of the invention is stable and accurate.

From chemistry, it is known that active oxygen, oxidant, is released from hydrogen peroxide in the presence of alkalizing agents or OH⁻ ions. OH⁻ is the expression of alkalinity and, as stated above, if this performs highly, total oxidation of the coloring pigments present in the mixture applied to the hair will be obtained. Consequently, as the color development of each coloring ingredient will have been total, the coloring obtained on the hair will undoubtedly be stable and in line with expectations.

In particular, according to laboratory tests, it has been found that an increase in some alkalizing products can lead to better coverage of white hair due to an increase in the development of oxygen, as the development of oxygen is dependent on alkalizing power.

In general, the following is found:
a more comfortable environmental, no emissions of irritating fumes or vapors, no particularly troublesome emissions of odors;
no irritation, itching, burning or reddening of the scalp.

Moreover, there is no damage to the hair itself: laboratory tests have shown how the hair treated with conventional dyes have a collapsed "triangular" or "quadrangular" structure, differing from the "round" structure that is found after using the dye of the invention.

According to the invention, the alkaline solution added to the dye, in its most general formula, consists of:
tri-N-propylamine;
arginine;
water;
an additional alkalizing agent selected from glucamine and bis (3-aminopropyl) dodecylamine.

In a preferred composition the amount expressed in percentage by weight in relation to the total of tri-N-propylamine is greater than 20%, and the pH value of said alkaline solution is ≥9.5

The best performances were obtained with an alkaline solution with pH of 10.5.

Some examples of alkaline solutions according to possible variants of the invention, expressed in percentage by weight in relation to the total, are set forth below.

EXAMPLE 1

Alkaline solution comprising:
tri-N-propylamine in a ratio of 40%;
arginine in a ratio of 30%;
glucamine in a ratio of 5%;
water in a ratio of 25%.

Said composition is characterized by a higher performance action in the immediate term, i.e. the first few minutes after application of the dye to the hair, having a high percentage of dominant alkalizing agent, i.e. 40% of tri-N-propylamine. However, as the application time continues, the alkalizing effect tends to decrease, losing part of the synergy with the other components.

EXAMPLE 2

Alkaline solution comprising:
tri-N-propylamine in a ratio of 40%;
arginine in a ratio of 20%;
bis (3-aminopropyl) dodecylamine in a ratio of 5%;
water in a ratio of 35%.

The operational tests and dyeing tests conducted directly on samples with this particular alkaline solution confirmed excellent coverage, unexpected silkiness and considerable colorfastness.

The particular alkalinity obtained for this formulation allows excellent opening of the hair scales, enabling the dye to penetrate into the hair follicle structure where it can oxidize and produce coloring. Indeed, it is known that the fastness/duration of the dye on a head of hair does not depend on the fact that the dye is deposited on the outside of the hair but that coloring develops inside the hair follicle structure.

In alternative variants attempts were made to reduce the percentage of the dominant alkalizing agent, i.e., tri-N-propylamine, testing alkaline solutions comprising:
tri-N-propylamine in a ratio of 28-32%;
arginine in a ratio of 18-22%;
glucamine in a ratio of 8-12%;
bis (3-aminopropyl) dodecylamine in a ratio of 3-7%;
water in a ratio of 33-37%.

The chemical-physical characteristics of alkaline solutions thus formulated are expressed in a synergy of alkaline values, where the activity of the OH⁻ ions is released in different times, i.e., oxidation takes place in steps so as to reach a pH value adequate for the purpose of dyeing the hair but, at the same time, completely tolerated by the skin. Excellent results are obtained specifically with the composition of the following example.

EXAMPLE 3

Alkaline solution comprising:
tri-N-propylamine in a ratio of 30%;
arginine in a ratio of 20%;
glucamine in a ratio of 10%;
bis (3-aminopropyl) dodecylamine in a ratio of 5%;
water in a ratio of 35%.

The use of tri-N-propylamine (also called tripropylamine) in the alkaline solution surprisingly allows permanent hair coloring to develop even with a relatively low percentage thereof, without the use of ammonia or ethanolamine (MEA). In fact, it is a highly alkaline substance and bonds optimally, allowing faster migration inside the hair. Moreover, it allows very effective coverage of the hair in suitable times, due to the lightness and simplicity of its molecular composition.

The invention claimed is:

1. A hair dye comprising:
a mixture comprising primary dyes, couplers, at least one alkalizing substance,
a buffer substance, and an antioxidant substance; and
at least one oxidizing agent,
wherein said alkalizing substance is contained in an alkaline solution comprising:
tri-N-propylamine;
arginine;
water; and
an alkalizing agent selected from glucamine and bis(3-aminopropyl)dodecylamine,
where a pH value of said alkaline solution is ≥ 9.5.

2. The hair dye according to claim 1, wherein the pH value of said alkaline solution is 10.5.

3. The hair dye according to claim 1, wherein the amount expressed in percentage by weight in relation to the total of tri-N-propylamine in said alkaline solution is greater than 20%.

4. The hair dye according to claim 1, wherein the components of said alkaline solution are contained with the following amounts expressed in weight percentage of the total:
tri-N-propylamine in a ratio of 40%;
arginine in a ratio of 30%;
glucamine in a ratio of 5%; and
water in a ratio of 25%.

5. The hair dye according to claim 1, wherein the components of said alkaline solution are contained with the following amounts expressed in weight percentage of the total:
- tri-N-propylamine in a ratio of 40%;
- arginine in a ratio of 20%;
- bis(3-aminopropyl)dodecylamine in a ratio of 5%; and
- water in a ratio of 35%.

6. The hair dye according to claim 1, wherein the components of said alkaline solution are contained with the following amounts expressed in weight percentage of the total:
- tri-N-propylamine in a ratio of 28-32%;
- arginine in a ratio of 18-22%;
- glucamine in a ratio of 8-12%;
- bis(3-aminopropyl)dodecylamine in a ratio of 3-7%; and
- water in a ratio of 33-37%.

7. The hair dye according to claim 6, wherein the components of said alkaline solution are contained with the following amounts expressed in weight percentage of the total:
- tri-N-propylamine in a ratio of 30%;
- arginine in a ratio of 20%;
- glucamine in a ratio of 10%;
- bis(3-aminopropyl)dodecylamine in a ratio of 5%; and
- water in a ratio of 35%.

* * * * *